United States Patent
Cooper

(10) Patent No.: US 8,091,585 B1
(45) Date of Patent: Jan. 10, 2012

(54) PNEUMATIC REGULATOR UNIT AND METHOD OF USE

(76) Inventor: Jeremy Cooper, Thousand Oaks, CA (US)

( * ) Notice: Subject to any disclaimer, the term of this patent is extended or adjusted under 35 U.S.C. 154(b) by 799 days.

(21) Appl. No.: 12/169,443

(22) Filed: Jul. 8, 2008

Related U.S. Application Data

(60) Provisional application No. 60/948,726, filed on Jul. 10, 2007.

(51) Int. Cl.
*F16K 11/24* (2006.01)
(52) U.S. Cl. ......................... 137/883; 606/186
(58) Field of Classification Search ................. 137/883; 606/186; 81/9.22
See application file for complete search history.

(56) References Cited

U.S. PATENT DOCUMENTS

| | | | | |
|---|---|---|---|---|
| 3,760,842 | A * | 9/1973 | Mikiya | 137/557 |
| 4,640,310 | A * | 2/1987 | Hartle et al. | 137/883 |
| 4,870,994 | A * | 10/1989 | Raymond | 137/899.4 |
| 5,261,704 | A * | 11/1993 | Araujo et al. | 285/9.1 |
| 5,303,733 | A * | 4/1994 | Nelson | 137/505.38 |
| 5,566,717 | A * | 10/1996 | Robert | 137/883 |
| 5,598,869 | A * | 2/1997 | Nelson | 137/505.11 |
| 5,957,393 | A * | 9/1999 | Price | 239/654 |
| 6,263,904 | B1 * | 7/2001 | Zdunek et al. | 137/375 |
| 6,305,049 | B1 * | 10/2001 | Koch | 16/110.1 |
| 6,340,034 | B1 * | 1/2002 | Arnott et al. | 137/883 |
| 6,352,546 | B1 | 3/2002 | Hill | |
| 6,834,666 | B2 * | 12/2004 | Murayama et al. | 137/269 |
| D613,572 | S * | 4/2010 | Nielsen et al. | D8/71 |

* cited by examiner

*Primary Examiner* — John Fox
(74) *Attorney, Agent, or Firm* — Ralph D. Chabot

(57) ABSTRACT

A pneumatic regulator unit housing having multiple output lines for connection to pneumatic devices such as needles used in creating tattoos is disclosed. The regulator unit comprises multiple outputs where each output is operatively connected to a respective pneumatic device such as a needle used for the tattooing operation.

5 Claims, 1 Drawing Sheet

PNEUMATIC REGULATOR UNIT AND METHOD OF USE

PRIORITY CLAIM

This application claims the benefit of U.S. Provisional Application No. 60/948,726, filed Jul. 10, 2007, the content of which is hereby incorporated by reference herein in its entirety for all purposes.

BACKGROUND OF THE INVENTION

My invention relates to the area of pneumatic regulators for control of compressed air.

Use of compressed air in tattooing is well known. Compressed air is used to power a pneumatic needle which delivers a colored dye below the skin layers of a human body. A recent example is described in U.S. Pat. No. 6,352,546 issued to Hill.

The tattooing procedure utilizes the use of a variety of colored inks as well as using various needle configurations which deliver ink in differing patterns. The typical procedure is to use a first colored ink and thereafter, disconnect the needle, purge the system of the first colored ink, attach a new needle having a different ink and continue the tattooing process.

For many tattooing procedures, a second or third, etc. color or needle configuration is necessary. In these cases, time is wasted in bleeding pressure from the compressed air line, disconnecting the first needle, connecting a subsequent needle having a different color/needle configuration, and then re-pressurizing the line. This longer than necessary procedure results in a longer period of time the customer has to endure the sometimes painful process. Further, contamination can occur and needle replacement can often cause infection if proper sanitary conditions are not properly maintained.

SUMMARY OF THE INVENTION

My invention is a multiple output gas regulator unit and method of use which can be designed for use by a tattoo artist.

My output regulator unit is a housing having an input coupling port for receiving air from a compressed air source and further comprises a plurality of output connectors to which a respective pneumatic device such as a needle can be operatively connected. In this way, the desired needle configuration and color is immediately available to the artist and no time is lost in disconnecting and re-connecting the air discharge line to the desired needle. My invention differs from what is available in the prior art in that all the necessary needles for a specific tattooing procedure can be immediately available to the artist during any point in the tattooing procedure.

The housing unit can be of any exterior configuration. Preferably, the housing unit is of a rectangular configuration. In the preferred embodiment, the input coupling port is located on one side with the output connectors located on a different side. The top surface of the unit displays the readout of the pressure gauge(s) and also has the necessary switches for operating the valves as discussed further herein.

A source for compressed air such as pressurized air tank is connected to my regulator unit by a gas/air input coupling port. The unit comprises a means for selectively controlling the flow of compressed air out through a selected output connector.

In a preferred embodiment, the means comprises an optional purge valve downstream of the input coupling port for line depressurization; a master on/off valve for permitting pressurized air through the downstream tubing of the unit; a plurality of output lines in parallel to one another; each output line having a respective on/off valve; an adjustable regulator valve positioned downstream of a respective on/off valve to more precisely control the downstream line pressure when the on/off valve is open; and, an output port for each downstream line for operatively coupling to a respective pneumatic needle. The on/off valve can be a mechanical valve such as a butterfly valve or an air control valve with manual return having a toggle switch. More preferably, the on/off valve is an electro-mechanical such as a solenoid valve and switch mechanism.

The pressure in the operative output line can be monitored by at least one pressure gauge. Preferably, each output line is monitored by a respective pressure gauge and most preferably, the pressure gauges are of the electronic display variety.

Both the input and output coupling ports can be with or without "press in fittings". Air/gas filters, commonly known in the art to separate water/moisture, can be positioned in-line upstream of the housing unit, or configured to be placed within the housing unit between the input port and check valve. The air/gas filter can incorporate an automatic drain for external draining.

The artist ready to begin the tattooing procedure operably connects a desired needle/ink combination to respective output ports. With all of the desired needle/ink combinations assembled and connected, the artist can selectively change between needle/ink combinations by closing the open output line on/off valve and opening another. The tattooing procedure thus becomes faster and more efficient.

My unit permits more than one artist to use the unit at the same time.

By way of example, when two artists are using the unit, with the master valve in the open position. Air is then available to each of the output lines. Opening the on/off valve for a respective output line will deliver air to the needle operatively connected to that line. In other words, multiple needles can be used for the tattooing procedure at the same time so long as the respective output line on/off valve is in the open position.

In another alternative two-user embodiment, the means for selectively controlling the flow of compressed air out through a selected output connector includes a second gas/air input coupling port is provided. The air supply can be coupled to both a first and a second input port. Besides the master valve described above, a second on/off valve is located downstream of the second input port. A third on/off valve is positioned in the line upstream of at least one of the parallel output streams. Preferably, this third master valve is positioned in the line upstream of at least two of the output lines. The operation works in the same manner as for the first alternative embodiment described above.

A low voltage power supply such as a battery is positioned within the housing and electrically connected to the solenoid valves and digital pressure displays. Power can also be provided by connection to an electrical outlet. Alternatively, the unit can be configured with manual valves and analog pressure gauges to eliminate the need for an electric power source. However, because of the complexity of the two-user embodiments, the electromechanical valves are preferred to be used.

DETAILED DESCRIPTION OF THE PREFERRED EMBODIMENT

Figure 1:
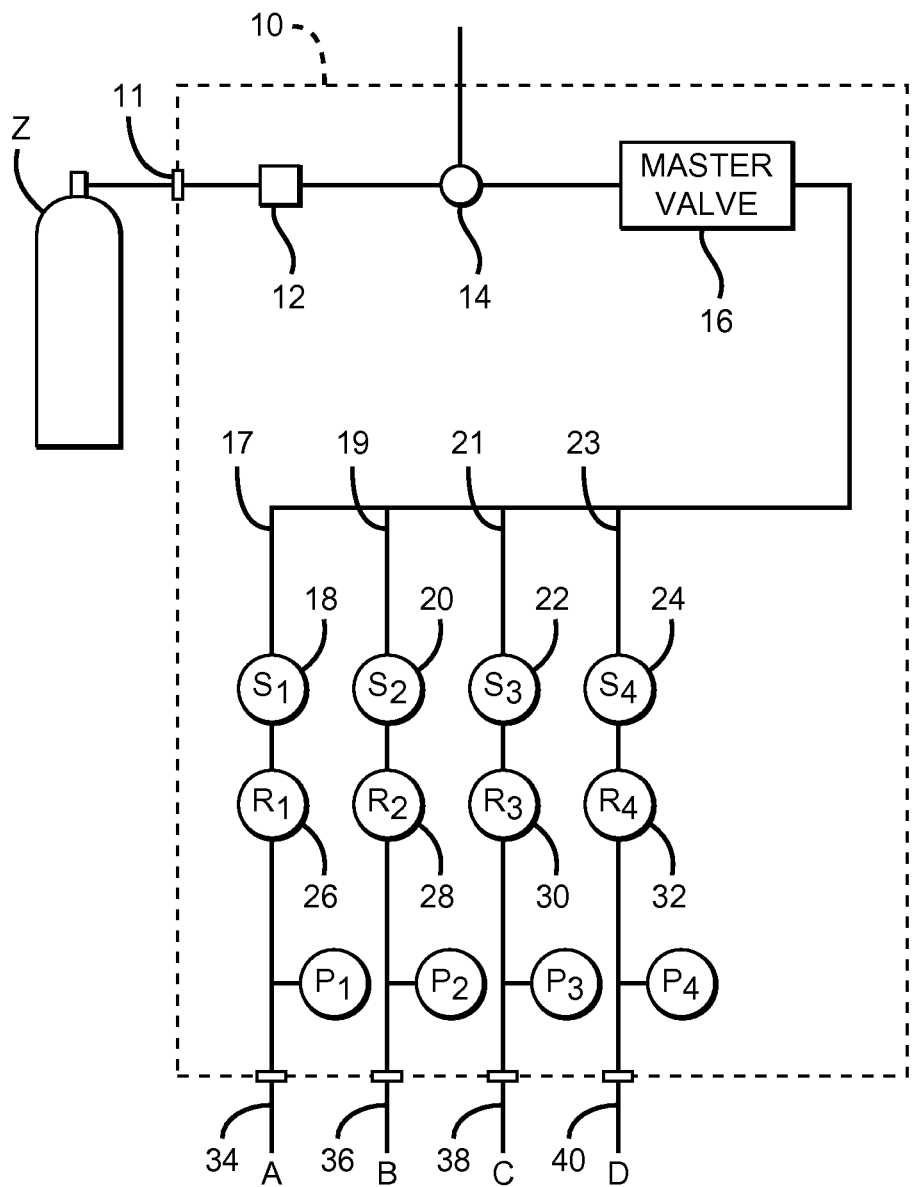
FIG. 1 is a flow chart illustrating possible air flow through my regulator unit.

FIG. 1 illustrates my regulator unit 10. FIG. 1 is not drawn to any scale and should therefore not be interpreted as a scaled drawing.

Unit 10 comprises a housing depicted by the rectangular dotted line. Input coupling port 11 is provided for operable connection to a compressed air source Z. The operable connection is tubing coupled on one end to source Z and on the other end to port 11. Within unit 10, compressed air flows through 5/32 inch tubing although substitute sizes can be used. In my preferred embodiment, an in-line filter (not shown) is positioned between source Z and unit 10. This operable connection is used to scrub and remove substantially all moisture that may be present in the compressed air prior to the air reaching unit 10. A purge valve 14 is located downstream of coupling port 11. An optional check valve 12 can also be provided.

A master solenoid valve and switch mechanism 16 which is positioned downstream of purge valve 14. This switch is used as a master control which can be used to immediately shut off the flow of air through unit 10. Downstream of valve 16 are a plurality of output lines. In FIG. 1, four output lines 17, 19, 21 and 23 are illustrated although more or less than four can be designed into unit 10 for operation.

Each output line includes a respective solenoid valve and switch mechanism 18, 20, 22, and 24. During the tattooing operation a single artist operating the unit should have one output line solenoid valve open and the others remain closed. Downstream of each output line solenoid valve is a respective adjustable valve or regulator 26, 28, 30, and 32. The purpose of the regulator is to more precisely control the flow of air through the output line.

Each downstream line has a respective output coupling port connector 34, 36, 38, and 40 which is used to operatively connect to a respective needle represented by A, B, C or D. As mentioned earlier for source Z, the operable connection is tubing coupled on one end to an output coupling connector and on the other end to a respective needle.

Once the needles are operably connected, the tattoo artist can selectively determine which needle to use, open the appropriate line by opening desired solenoid valve 18, 20, 22, or 24 and regulate air flow using the respective controlling regulator, 26, 28, 30, or 32.

Each output line has a digital readout pressure gauge P1, P2, P3 and P4 for assisting the artist in determining the appropriate pressure required.

In the method of use, a pressurized air supply Z is connected to unit 10 at input port 11. Depending on the complexity of the tattoo design to create, the artist will determine whether more than one needle/ink combination is required and assemble the necessary needle/ink combinations represented by A, B, C, D, and operatively connect each combination to a respective output stream. The artist would switch solenoid valve 16 into the open position and then select the desired needle/ink combination A, B, C, or D by opening the corresponding solenoid valve 18, 20, 22, or 24 and controlling the pressure using respective regulator 26, 28, 30 or 32. When the artist desires to use a different needle/ink combination, the artist closes the output line solenoid valve currently open, and opens the now desired output line solenoid valve and the tattooing procedure continues in this manner until complete.

A power supply (not shown) is used to provide electrical power for operation of all solenoid valves as well as digital pressure gauges.

Where more than one tattoo artist uses my regulator unit at the same time, the procedure as above remains essentially the same. The only difference is that more than one solenoid valve 18, 20, 22, and 24 will be open at the same time providing air flow to two of the respective needles A, B, C and D.

I claim:

1. A regulator unit for operatively connecting a compressed air source to at least one pneumatic device comprising:
    an input coupling port for receiving compressed air;
    a purge valve located downstream of said input coupling port;
    a master solenoid valve and switch mechanism located downstream of said purge valve;
    a plurality of output lines connected in parallel downstream of said master solenoid valve; each of said output lines connected to a respective output coupling port configured for operable connection to a desired external pneumatic device; and,
    each of said output lines having a solenoid valve and switch mechanism and an adjustable regulator valve located downstream of the solenoid valve and switch mechanism for adjustably controlling the flow of air through said respective output line; and the line pressure downstream of the solenoid valve and switch mechanism monitored by at least one pressure gauge.

2. A regulator unit for operatively connecting a compressed air source to at least one pneumatic device comprising:
    an input coupling port for receiving compressed air;
    a purge valve located downstream of said input port;
    a master on/off valve located downstream of said purge valve;
    a plurality of output lines connected in parallel downstream of said master valve; each of said output lines connected to a respective output coupling port configured for operable connection to a desired external pneumatic device;
    each of said output lines having an on/off valve and switch mechanism and an adjustable regulator valve located downstream of the on/off valve for adjustably controlling the flow of air through said respective output line and the line pressure downstream of the solenoid valve and switch mechanism monitored by at least one pressure gauge.

3. The regulator unit of claim 2 where said on/off valves are mechanical valves.

4. The regulator unit of claim 2 where said on/off valves are electro-mechanical valves.

5. A method for tattooing comprising the steps of:
    providing a regulator unit for tattooing comprising:
        an input coupling port for receiving compressed air;
        a purge valve located downstream of said input coupling port;
        a master on/off valve located downstream of said purge valve;
        a plurality of output lines connected in parallel downstream of said master on/off valve; each of said output lines connected to a respective output coupling port configured for operable connection to a desired external pneumatic needle;
        each of said output lines having a respective pressure gauge, an on/off valve and a regulator valve located downstream of the output line on/off valve for adjustably controlling the flow of air through said respective output line;
    operatively connecting a pressurized air supply to said regulator unit;
    operatively connecting a respective pneumatic needle to each of said plurality of output coupling ports;
    selecting a pneumatic needle for the tattooing operation by opening said respective output line on/off valve and adjusting the air flow through the respective output line as necessary using said respective regulator valve.

* * * * *